(12) United States Patent
Auxepaules et al.

(10) Patent No.: US 7,341,593 B2
(45) Date of Patent: Mar. 11, 2008

(54) PROSTHETIC ACETABULAR CUP INSERTER

(75) Inventors: Arnaud Auxepaules, Saint-Aubin-Sur-Mer (FR); Nicolas Delogé, Douvres-La-Deliverande (FR)

(73) Assignee: Benoist Girard SAS (FR)

( * ) Notice: Subject to any disclaimer, the term of this patent is extended or adjusted under 35 U.S.C. 154(b) by 149 days.

(21) Appl. No.: 11/072,583

(22) Filed: Mar. 4, 2005

(65) Prior Publication Data

US 2005/0228395 A1    Oct. 13, 2005

(30) Foreign Application Priority Data

Mar. 5, 2004    (GB) ................. 0405059.7

(51) Int. Cl.
*A61F 2/46*    (2006.01)

(52) U.S. Cl. ....................................... 606/91

(58) Field of Classification Search .......... 606/81, 606/91, 99
See application file for complete search history.

(56) References Cited

U.S. PATENT DOCUMENTS

| | | | |
|---|---|---|---|
| 3,859,992 A * | 1/1975 | Amstutz | 606/91 |
| 4,293,962 A | 10/1981 | Fuson | |
| 4,305,394 A | 12/1981 | Bertuch, Jr. | |
| 4,632,111 A | 12/1986 | Roche | |
| 5,116,339 A | 5/1992 | Glock | |
| 5,169,399 A | 12/1992 | Ryland et al. | |
| 5,395,188 A | 3/1995 | Bailey et al. | |
| 5,486,181 A * | 1/1996 | Cohen et al. | 606/91 |
| 5,540,697 A | 7/1996 | Rehmann et al. | |
| 5,571,111 A | 11/1996 | Aboczky | |
| 5,683,399 A | 11/1997 | Jones | |
| 5,902,107 A | 5/1999 | Lowell | |
| 5,908,423 A | 6/1999 | Kashuba et al. | |
| 5,928,287 A * | 7/1999 | Keller | 623/22.21 |
| 5,954,727 A | 9/1999 | Collazo | |
| 6,022,357 A * | 2/2000 | Reu et al. | 606/99 |
| 6,063,124 A | 5/2000 | Amstutz | |
| 6,093,184 A | 7/2000 | Campbell et al. | |
| 6,174,313 B1 | 1/2001 | Bonutti | |
| 6,200,306 B1 | 3/2001 | Klostermeyer et al. | |

(Continued)

FOREIGN PATENT DOCUMENTS

WO    WO-01/06964 A    2/2001

(Continued)

*Primary Examiner*—Eduardo C. Robert
*Assistant Examiner*—Nicholas Woodall
(74) *Attorney, Agent, or Firm*—Lerner, David, Littenberg, Krumholz & Mentlik, LLP (57) ABSTRACT

An acetabular cup shell inserter has a first end with a handle and a wire coupling element. The inserter has a shell insertion end opposite the first end having a radial expandable element for contacting an inner surface of the acetabular cup shell. A tubular portion is provided extending between the handle end and the insertion end. The tubular portion may be curved. A wire having a first end coupled to the coupling element at the first end is provided. The wire extends through the tubular portion and into the insertion end, the wire having a second end coupled to a moveable element for expanding the expandable element. The inserter includes a system for applying tension to the wire, such as by moving the wire in a direction towards the first end, the tension causing the expandable element to expand and grip the inner surface of the shell.

32 Claims, 9 Drawing Sheets

U.S. PATENT DOCUMENTS

| | | |
|---|---|---|
| 6,447,518 B1 | 9/2002 | Krause et al. |
| 6,468,281 B1 * | 10/2002 | Badorf et al. ............ 606/91 |
| 6,613,085 B1 | 9/2003 | Anderson et al. |
| 2003/0050645 A1 | 3/2003 | Parker et al. |
| 2003/0229356 A1 | 12/2003 | Dye |
| 2004/0153063 A1 | 8/2004 | Harris |
| 2004/0186586 A1 | 9/2004 | Seyer et al. |
| 2006/0149285 A1 * | 7/2006 | Burgi et al. ............ 606/99 |

FOREIGN PATENT DOCUMENTS

| | | |
|---|---|---|
| WO | WO-2004/010882 A1 | 2/2004 |

* cited by examiner

PROSTHETIC ACETABULAR CUP
INSERTER

BACKGROUND OF THE INVENTION

This invention relates to a prosthetic acetabular cup inserter which is particularly, although not exclusively, applicable for minimally invasive surgery (MIS) with small incisions. The inserter can also be used to orient the cup outer shell in the acetabulum and to impact it. The outer shell generally receives a polyethylene or ceramic bearing which in turn receives the spherical head of a femoral component. The invention allows the inserter to have a curved shape although the invention can be applied to inserters with a substantially axially straight shape.

WO 2004/010882 shows a surgical impactor which is intended for engagement with a threaded implant. The cup holder is provided with a collet which carries a screw thread and the collet can be opened or closed by operation of a tapered cam. The cam is resiliently biased into its operative position to open the collet to collapse which reduces or collapses a screw thread to detach the impactor from the implant.

A fundamental problem with this construction is that the cam is not forceably held in its operative position but merely relies upon a spring so that the cam can move backwards against the spring in certain circumstances thus reducing the grip on the implant. Moreover, the available area of the collet for engaging the implant is restricted by the cover which must extend over the collet to locate it in place.

Curved acetabular cup impactors/inserters/reamers are shown in U.S. Patent Publications 2003/0050645, 2003/0229356 and 2004/0153063.

Straight impactors showing devices for gripping the outer shell of the acetabular cup system are shown in U.S. Pat. Nos. 4,632,111, 5,169,399, 5,571,111, 5,540,697 and 5,954,727.

U.S. Pat. No. 4,632,111 shows apparatus for positioning a prosthetic acetabular cup within an acetabulum and relies upon an expandable elastomeric annular collar. The collar is expanded by operation of a hand retainer nut which acts on a threaded stem to provide pressure against the annular collar so that it can be compressed and its diameter increased to grip the inner surface of the cup to be implanted.

It would be very difficult to use this device where there is little available room for the surgeon to operate, especially for minimally invasive surgery (MIS) with a short incision. The present invention is intended to overcome the difficulties of both the above earlier disclosures and to provide a prosthetic acetabular cup inserter which is easier to operate.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

According to the present invention a prosthetic acetabular cup inserter includes an adjustable cup holder having a resilient ring which can be expanded to grasp the cup outer shell with which it is to be used by operation of an elongated flexible element by a tensioning device which tensions, for example, a cable which causes the resilient ring to expand.

Thus, the adjustable cup holder can be carried on an operating handle and the elongated flexible element can be operable from the handle. In a preferred embodiment, the handle is connected to the adjustable cup holder by an extension and this can be curved or substantially straight. The elongated flexible element may conveniently be carried within the extension.

In a preferred embodiment, the tension is applied to the elongated flexible element by an operating element carried on a ramp or screw thread so that rotation thereof causes lengthwise movement of the elongated flexible element.

In an alternative embodiment, the force can be applied to the elongated flexible element by a pivoted trigger mechanism, angular movement of which causes lengthwise movement of the elongated flexible element.

A device can be included for adjusting the operative length and tension of the elongate flexible element. In a preferred arrangement the trigger mechanism can include a rotatable cam which can be operated to apply the tension to the elongate flexible element.

The adjustable cup holder can include a backing member, a movable operating member and a resilient deformable member which is deformed to grasp and inner surface of the cup to be inserted when the movable operating member is moved in relation to the backing member. The resilient ring can be made from an elastomeric material and can be axially compressed to cause it to expand radially to grip the cup.

A system can be included for adjusting the operative length and tension of the elongate flexible element.

In a preferred arrangement the trigger mechanism can include a rotatable cam which can be operated to apply the tension to the elongate flexible element.

The adjustable cup holder can include a backing member, a movable operating member and a resilient deformable member which is deformed to grasp an inner surface of the cup to be inserted when the movable operating member is moved in relation to the backing member.

The resilient ring can be made from an elastomeric material and can be axially compressed to cause it to expand radially to grip the cup.

The adjustable cup holder can include a backing member and a movable operating member to which the flexible element is connected and between which the resilient ring is located so that it is axially compressed when the movable operating member is moved towards the backing member when tension is applied to the flexible element. Thus, the resiliently deformable member may be arranged to grasp the inner rim of the cup or an area adjacent thereto.

In an alternative construction the resiliently deformable member can be in the form of split ring and the movable operating member can include a tapered portion which acts against the inner surface of the ring to cause it to expand to engage and grip the cup to be inserted.

The backing member can be removably secured to the handle or extension thereof to allow the cup holder to be removed and the backing member can be provided with a system for securing it in a predetermined angular position in relation to the axis of the handle and/or extension thereof.

In the above constructions one end of the elongated flexible element can be secured to the movable operating member and the other end secured to the operating element carried on the operating handle or extension. A system can be included to apply a first tension to the flexible cable to hold the backing member and movable operating member in position in the adjustable cup holder and then to apply a second tension to cause the resilient ring to expand. The first tension can be achieved in a first position of the trigger and the second tension when the trigger is in a second position. The elongated flexible element can be made of any suitable material and in a convenient construction is in the form of a metal cable.

The invention also includes a prosthetic acetabular cup inserter as set forth above including in combination therewith one or more alternative cup holders which have different dimensions and are for use with cups of different dimensions from the first and which can be fitted in place of the first cup.

It will be appreciated that the use of such an elongated flexible element provides the designer with a wide range of possibilities due to the ability of the cable to extend around curves and corners between an operating position, for example on the handle of the device, and the adjustable cup holder, and the use of the flexible element in tension ensures a sufficiently powerful operation for the expansion of the resilient ring.

BRIEF DESCRIPTION OF THE DRAWINGS

The invention can be performed in various ways and two embodiments will now be described by way of example and with reference to the accompanying drawings in which.

DETAILED DESCRIPTION

As shown in FIGS. 1 to 12 the preferred prosthetic acetabular cup inserter, according to the present invention, comprises an adjustable cup holder 1 which can be operated to grasp the cup 2 with which it is to be used from a position remote from the cup holder 1 through an elongated flexible element 3 which is in the form of a steel cable.

Figure 1:
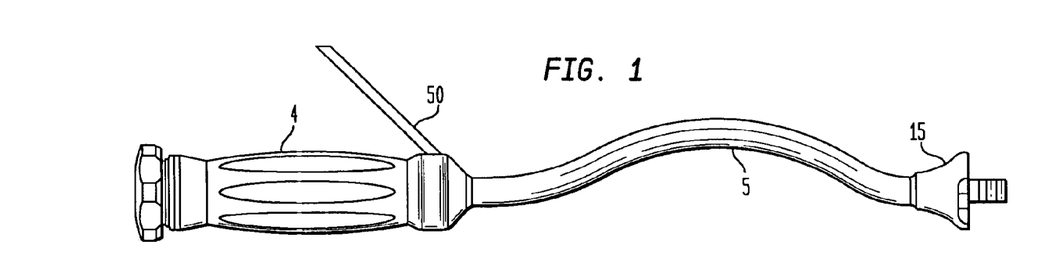
FIG. 1 is a side elevation of a prosthetic acetabular cup inserter but without an adjustable cup holder.
Figure 2:
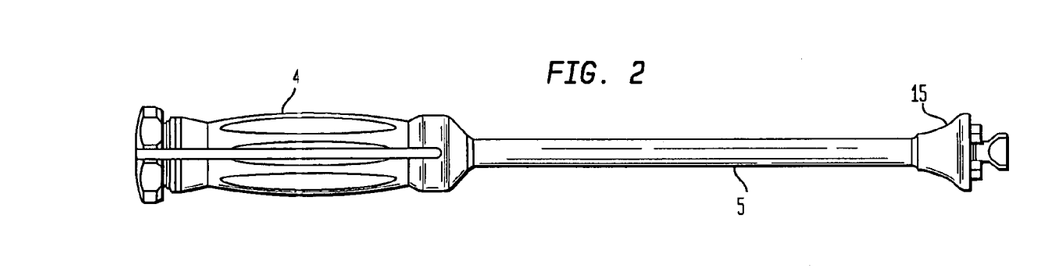
FIG. 2 is a plan view of the cup inserter shown in FIG. 1.
Figure 3:
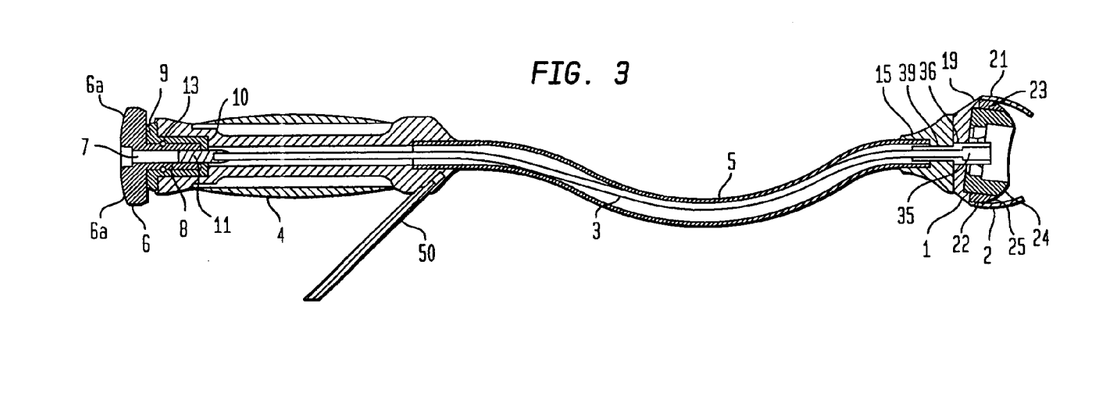
FIG. 3 is a cross-sectional side elevation of the other side of the inserter from that shown in FIG. 1 and with the adjustable cup holder in place on a prosthetic acetabular cup.

The adjustable cup holder 1 is carried on an operating handle 4 which can be rubberized and from which the flexible element 3 is operated. The free end of handle 4 may have a knob 6 with a striker area 6a. The handle 4 is connected to the adjustable cup holder by a hollow extension 5 within which the flexible element 3 is carried. As will be seen from the drawings the extension is of a curved shape to assist the surgeon during surgery.

A tension force is applied to the flexible element 3 by an operating element 6 which is in the form of a grooved knob and which has a screw threaded axial bore 7. An extended portion 8 of the knob 6 is located in a top hat shaped bearing 9 and in which it can freely rotate. The inner end of the bearing 9 is closed but has a shaped bore 10, provided with three flats which are angularly spaced apart by 120°, and within which a shaped nipple 11 (shown in FIGS. 5 and 6) provided on the flexible element 3 can slide but not rotate. From FIGS. 5 and 6 it will be seen that the shaped nipple is substantially cylindrical apart from a set of three flats 12 which are angularly spaced apart by 120° and this portion of the nipple 11 also carries a screw thread which can co-operate with the screw thread in the bore 7 on the operating knob 6. Thus, rotation of the operating knob 6 will cause the screw threaded nipple to move backwards and forwards in the screw threaded bore 7 and it is held against rotation by the flats 12 acting against the flats in shaped bore 10 in the bearing 9. Rotational movement of the knob 6 can therefore be in a direction to create a tensional force in the flexible element 3.

Figure 4:
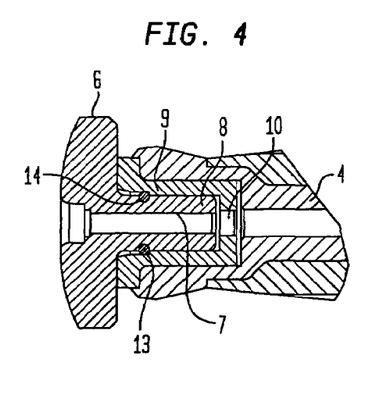
FIG. 4 is an enlarged cross-sectional elevation of part of the inserter shown in FIGS. 1 to 3.
Figure 5:
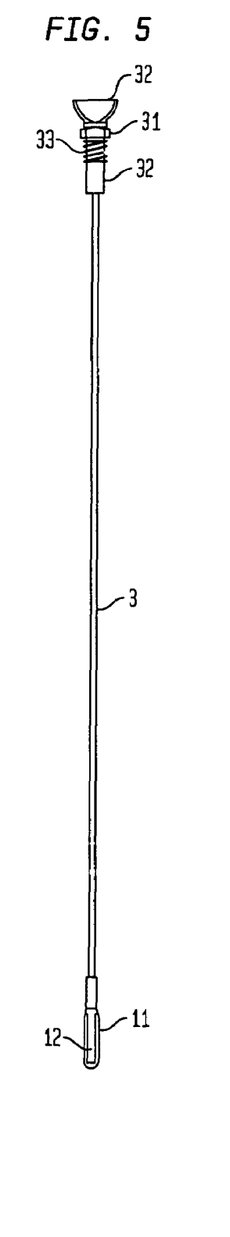
FIG. 5 is a plan view of the elongated flexible element used in the construction shown in FIG. 3.

As shown in FIG. 4, in order to facilitate location of the extended portion 8 in the bearing 9 a ring 13 is provided in a groove 14 which holds it in place when the flexible element 3 is not assembled, but which can be dismantled for cleaning.

Figure 7:
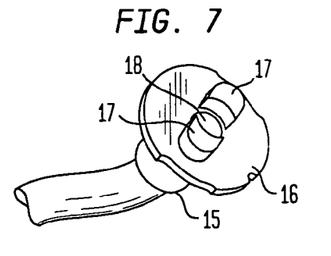
FIGS. 7 to 11 are pictorial isometric views showing how the various parts of the adjustable cup holder are assembled together.
Figure 8:
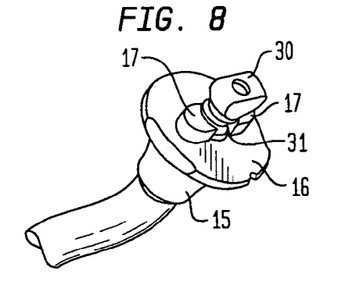

The end of the extension 5 spaced away from the handle 4 includes a substantially conically shaped end piece 15 which is rigidly secured to the hollow extension 5. As is best seen in FIGS. 7 and 8 the end piece 15 has a flat substantially circular bearing surface 16 which is provided with a pair of spaced apart shaped abutments 17 and which are arranged diametrically opposed to each other on each side of a bore 18 which communicates with the bore of the hollow extension 5.

A backing member in the form of a pressure plate 19 has a shaped opening 20 adapted to fit over the abutments 17 which act to prevent plate 19 from rotating on the end piece 15. The backing plate 19 has an outer rim 21 which is shaped and adapted to align with the outer rim 22 of the acetabular cup shell to be inserted. The inner edge of the outer rim 21 of the plate 19 is shaped to receive a resiliently deformable member in the form of a flexible ring 23. This can be square, rectangular or circular shaped as required. The outer diameter of flexible ring 23 is very slightly less than the inner diameter of the rim 22 of the cup 2 so that it can extend over it.

The flexible ring 23 is located on a movable operating member 24 which has an outer rim 25 shaped to extend over and engage the outer rim of the ring 23. The movable operating member 24 is also provided with a shaped opening 26 and which is of substantially the same shape and dimensions as the opening 20 in the backing member 19.

Figure 6:
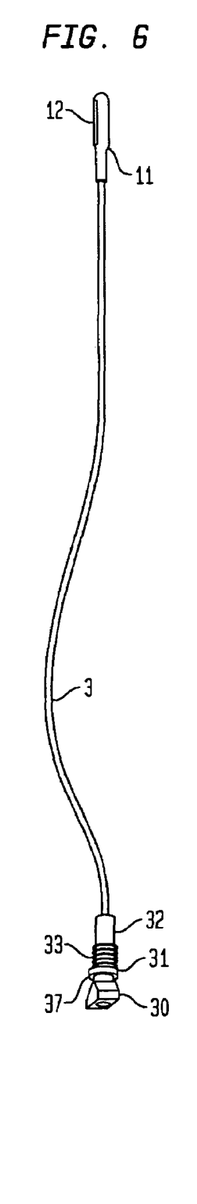
FIG. 6 is a pictorial isometric view from the other end of the elongated flexible element as shown in FIG. 5.

As seen in FIG. 6, the end of the flexible element 3 displaced from the nipple 11 carries a shaped locking head 30 which has a shaped part-circular collar 31 and a cylindrical stem portion 32. The locking head 30 has a bore 36 which also extends through the cylindrical portion 32 and the outer end of which is substantially rectangular. This engages with a substantially rectangular nipple 35 (and shown in FIG. 3) and prevents the head 30 from rotating on the element 5. The collar 31 is shaped to locate within the abutment 17 with its flat sides 37 aligned with the edges 38 of the abutments, as will be clearly seen from FIG. 9, and so that when the backing plate 19 is placed in position over the abutments 17 it will prevent rotation of the collar 31 on the head 30 and cylindrical extension 32. The spring 33 engages against a shoulder 39 in the bore 36 in the conically shaped end 15 so that the head 31 is biased outwardly from the extension 5 into the position shown in FIG. 9.

The parts are assembled together as shown in FIGS. 7, 8, 9, 10 and 11. FIG. 7 shows the end piece 15 ready to receive the flexible element 3. This is inserted so that the end carrying the nipple 11 is pushed through the extension and handle and until it engages with the screw threaded bore 7 in the operating knob 6. Rotation of the operating knob in the appropriate direction now causes the nipple 11 to move up the bore 7.

Figure 9:
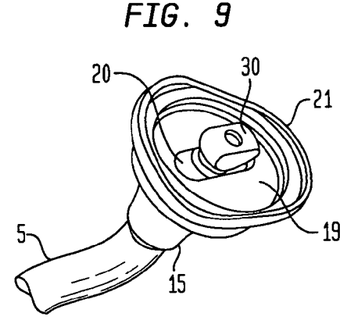

With the head 30 in position, as shown in FIG. 8, the backing plate 19 can be added by passing it over the projections 17 where it also acts to prevent rotation of the collar 31 as shown in FIG. 9.

Figure 10:
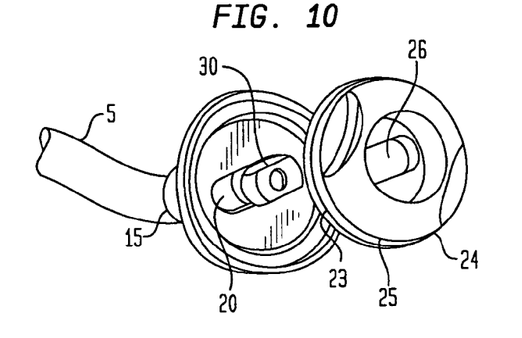
Figure 11:
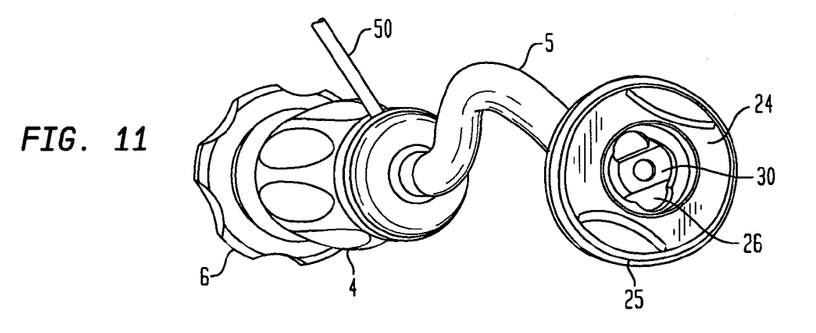

The movable operating member 24 is now placed in position, as indicated in FIG. 10, and is then rotated through 90° so that its opening 26 lies at right angles to the head 31 and thus locks the assembly together, as shown in FIG. 11.

The edge of the inner rim 25 now rests against the flexible deformable ring 23 which has been placed in position prior to the movable operating member 24.

With the parts in the position indicated above the cup 2 to be inserted is placed over the rim of the ring 23 and the operating knob 6 is rotated appropriately which causes a tension and axial movement of the flexible element 3 thus pulling the movable operating member 24 against the resiliently deformable ring 23 so that it is compressed and is forced radially outwardly against the inner surface of the outer edge of the cup thus grasping the rim of the cup and holding it in position in relation to the inserter, as shown in FIG. 3.

The cup can now be inserted in the acetabulum as required and the cup can also be held in this position if impaction is required.

With the cup positioned it can be easily released merely by rotating the operating knob 6 appropriately which will release the pressure on the resiliently deformable ring 23 and allow the inserter to be removed.

Figure 12:
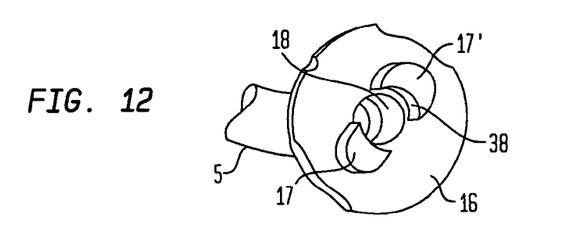
FIG. 12 is an isometric view of an alternative construction of part of the adjustable cup holder.

FIG. 12 shows an alternative embodiment in which the same reference numerals are used to indicate similar parts but in this arrangement the shaped abutments 17 are of different dimensions, one, 17', being larger than the other. The shaped opening 20 is shaped to accommodate the abutments 17 to ensure that the pressure plate 19 can only be fitted in one predetermined position. This construction is for use with prosthetic cups which have a particular anatomic shape and which require insertion in a particular position in the acetabulum.

Figure 13:
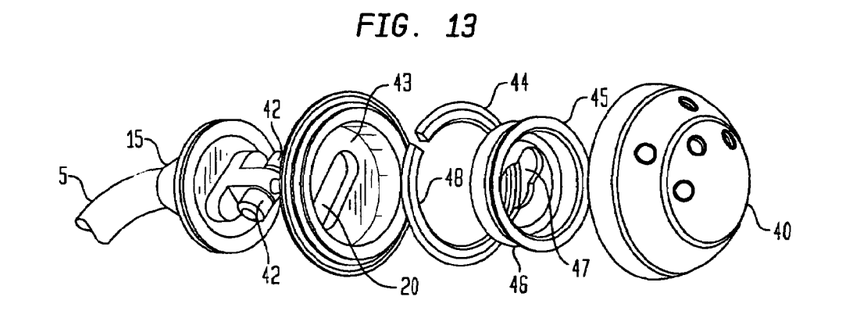
FIG. 13 is a pictorial exploded isometric view of the various parts of another alternative construction of adjustable cup holder.
Figure 14:
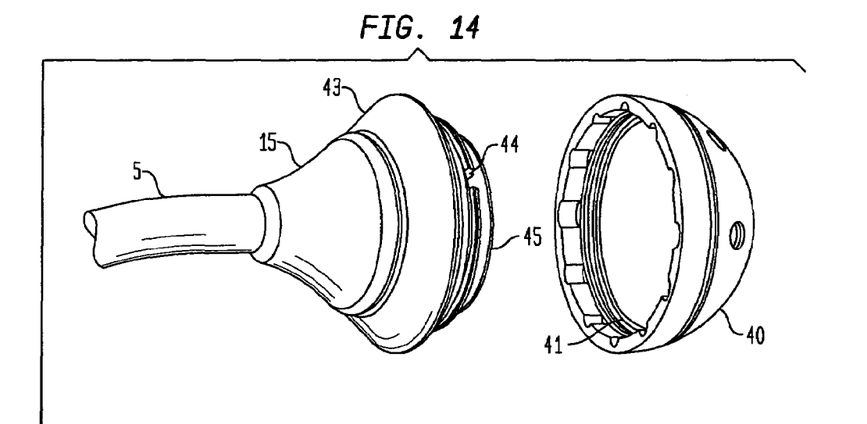
FIG. 14 is an isometric view showing the adjustable cup holder shown in FIG. 13 ready to receive the acetabular cup with which it is to be used.
Figure 15:
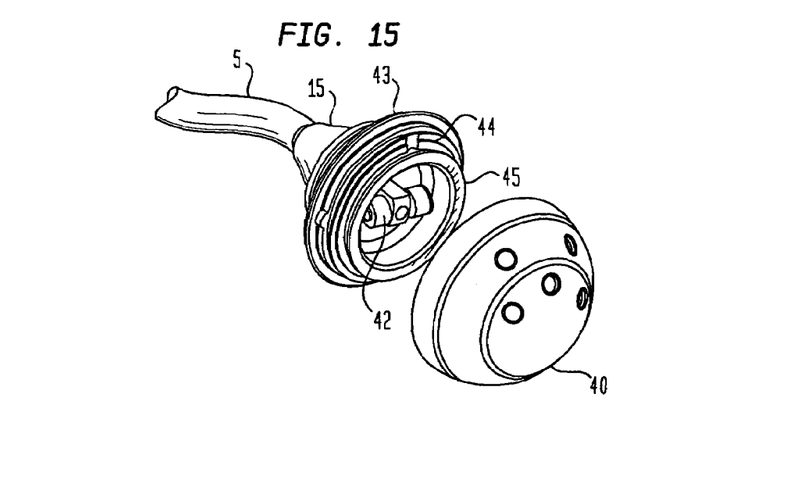
FIG. 15 is another isometric view of the adjustable cup holder shown in FIG. 13 ready to receive the acetabular cup.

FIGS. 13, 14 and 15 show an alternative embodiment in which the same principles are employed as that set forth in FIGS. 1 to 12 but in this construction the adjustable cup holder is designed to operate with a cup 40 which has an internal groove 41 displaced inwardly from its immediate inner rim which carries a ring of depressions. With this construction the shape of the conical end 15 of the apparatus is similar to that described with regard to FIGS. 1 to 12 but the shaped head 30 on the flexible element 3 is replaced by a head carrying a pair of cylindrical abutments 42. A backing or pressure member 43 of similar construction to but of different shape to that shown in FIG. 9 is employed and located on this is a circlip or split ring 44 which replaces the deformable ring 23 shown in FIGS. 1 to 12. The circlip can be made of metal or any other suitable material. The removable operating member in this construction is in the form of a dished member 45 which has a conical outer wall 46 and a shaped opening 47 which is dimensioned to pass over the abutments 42. The shape of the abutments 17 can be as shown in FIG. 12.

The assembly is placed together in a similar manner to that described with regard to the earlier construction and the removable operating member 45 is again rotated through 90° to hold it in position. When the operating knob 60 is rotated the flexible element 3 again acts to pull the removable operating member 45 towards the backing member 43 but in this case the tapered sides of the operating member engage the inner surface 48 of circlip 44 forcing it apart. Thus, when the cup 40 is placed on the assembly operation of the flexible element 3 causes the circlip 44 to expand into the groove 41 on the cup 40 and thus hold it in position. The cup can be released by again operating the knob 6.

As shown in FIG. 1 a guide 50 can also be provided on or adjacent the handle to assist the surgeon.

Figure 16:
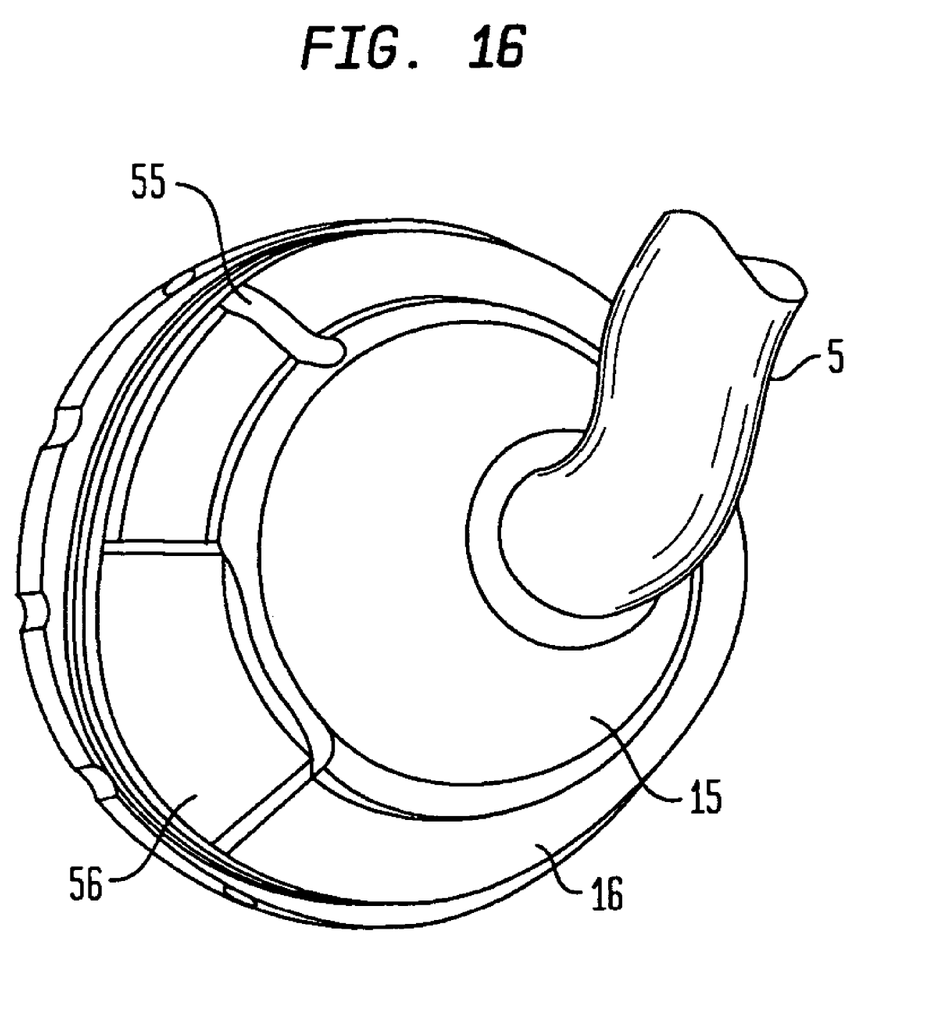
FIG. 16 is an isometric view of the adjustable cup holder shown in FIGS. 1 to 12 or 12 to 15.

FIG. 16 shows how the rear face of the pressure plate 19 can be marked with a landmark 55 to indicate the position of a trial cup (not shown) to the definitive cup 2 to be inserted using a bistoury marking on the rim of the acetabulum. Reference numeral 56 indicates an area to position the trial cup following the anterial rim of the acetabulum. The markings are desirable for use with cups which have a particularly shaped rim.

Figure 17:
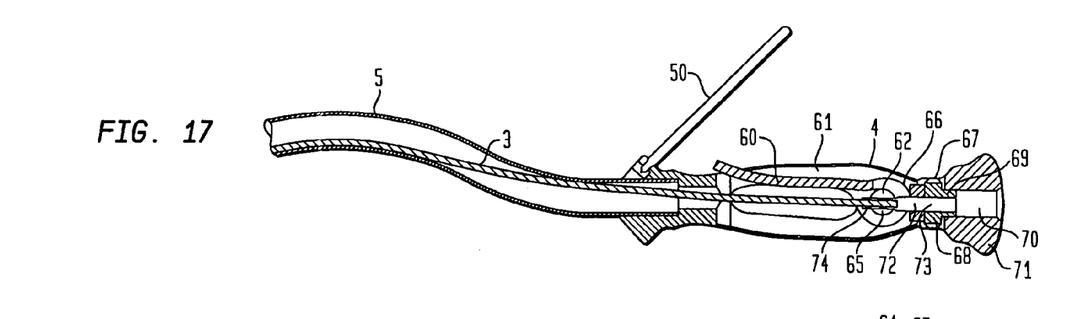
FIG. 17 is a cross-sectional side elevation of part of another alternative construction.
Figure 18:
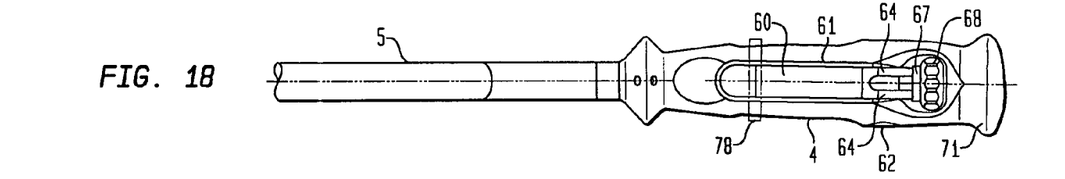
FIG. 18 is a plan view from above of the construction shown in FIG. 17.
Figure 19:
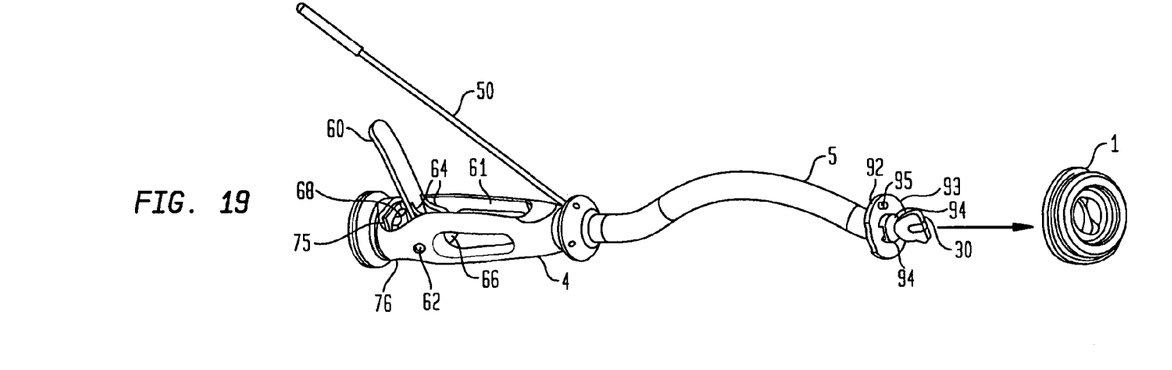
FIG. 19 is an isometric view of the construction shown in FIGS. 17 and 18.

FIGS. 17 to 19 show another alternative construction in which the same reference numerals are used to indicate similar parts to those shown in FIGS. 1 to 12.

In this construction a trigger mechanism is employed the pivotal movement of which is used to tension the flexible element 3. The trigger mechanism comprises an operating trigger lever 60 which is located within a slot 61 in the handle 4 and carried on a pivot pin 62 which extends transversely across the handle 4. The trigger lever 61 has a pair of flanges 64 each of which has a bore 65 to accept one of the pivot pin 62. The flanges 64 each have a cam surface 66 which extends around the end of the trigger lever 60. Thus, when the lever 60 is pivoted about the pivot pin 62 the cam surfaces 66 are also rotated. Cam surfaces 66 bear against a cylindrical bearing block 67 carried on an adjustment hand wheel 68. The hand wheel 68 has an extension 69 which locates in a bearing bore 70 provided in a handle end cap 71.

The end of the flexible element 3 is provided with a screw threaded nipple 72 which is carried in a screw threaded bore 73 in the adjusting wheel 68 and extends through an opening 74 in the pivot pin 62 and between the cam flanges 64.

As will be seen from FIG. 19 the handle 4 is cut away at 75 and 76 to provide an extension of the slot 61 to enable the hand wheel 68 to be rotated by the operator. The adjustable cup holder 1 can be similar to that shown in FIGS. 1 to 12 and the flexible element 3 can be attached in a similar manner, preferably however an alternate cup holder construction is used which is shown in FIGS. 19 to 28 as further described below.

To operate the trigger mechanism the trigger is first lifted to the position shown in FIG. 19. In this position the height of the cam surface is their lowest so that there is the maximum relaxation of the flexible element 3. This enables the cup to be placed in position on the cup holder. The lever is now rotated in an anticlockwise direction when viewed in FIG. 17 which moves the cam surfaces round their highest position which in turn forces the bearing block 67 towards the right (as shown in FIG. 17) thus tensioning the flexible element 3 which is connected to the bearing block 67 and the hand wheel 68, the axial movement being accommodated in the bore 70. The tension of the flexible element 3 is sufficient for the flexible ring 23 in the cup holder 1 to grasp the cup. The trigger mechanism can also be employed with the cup holder construction shown in FIGS. 13 to 16.

The applied tension at the closed position of the trigger, that is in the position shown in FIG. 17, can be adjusted by rotating the hand wheel 68. This can be rotated on the threaded nipple 72 which will cause the nipple to move axially in either direction depending upon the direction of rotation of the hand wheel. The effect is to vary the operative length of the flexible element 3 and to increase or decrease the applied tension.

The hand wheel can thus be used when different sized cups are employed which, depending upon their dimensions, may require slightly more or less movement of the resilient ring to grasp the cup.

If required the trigger mechanism can include a locking mechanism to allow it to be locked in the position shown in FIG. 17. This, for example, can be in the form of a simple rotating clasp indicated by reference numeral 78 and shown in broken lines in FIG. 18.

Figure 20:
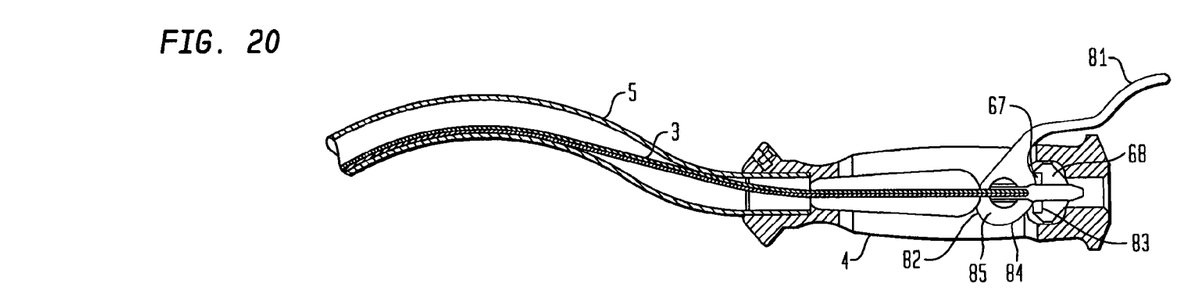
FIG. 20 is a sectional side elevation of an alternative construction with an operating trigger lever in a free position and in which the handle can receive the adjustable cup holder.
Figures 21, 22:
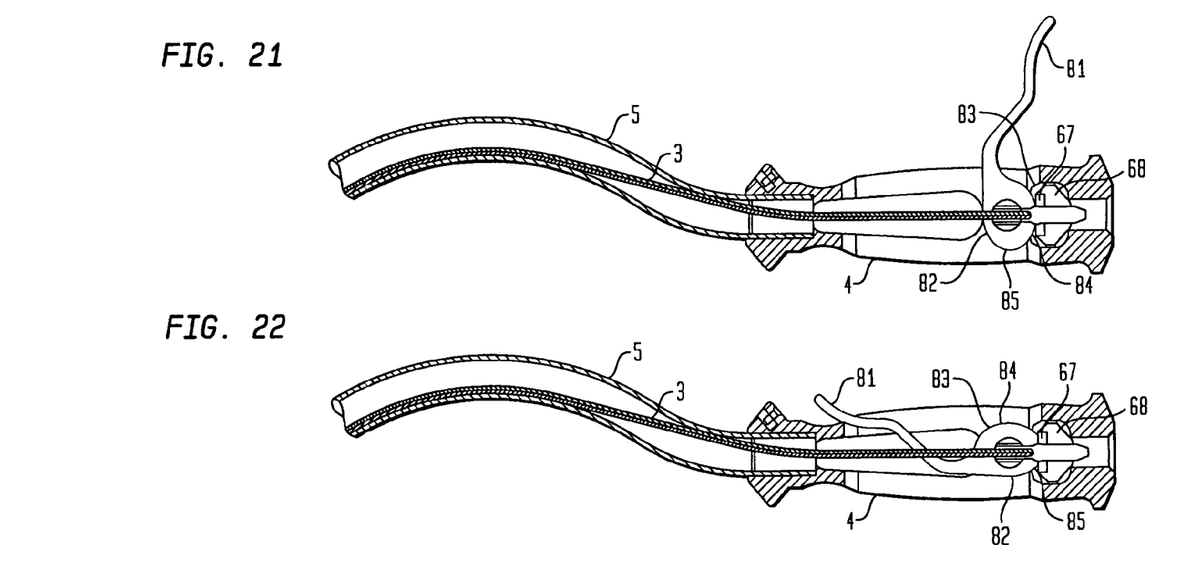
FIG. 21 is a view similar to FIG. 20 of the same construction with the operating trigger lever in a position to cause a first tension to hold the adjustable cup holder in position.
FIG. 22 is a view similar to FIGS. 20 and 21 of the same construction with the operating trigger lever in a position to grasp the cup to be inserted.
Figure 23:
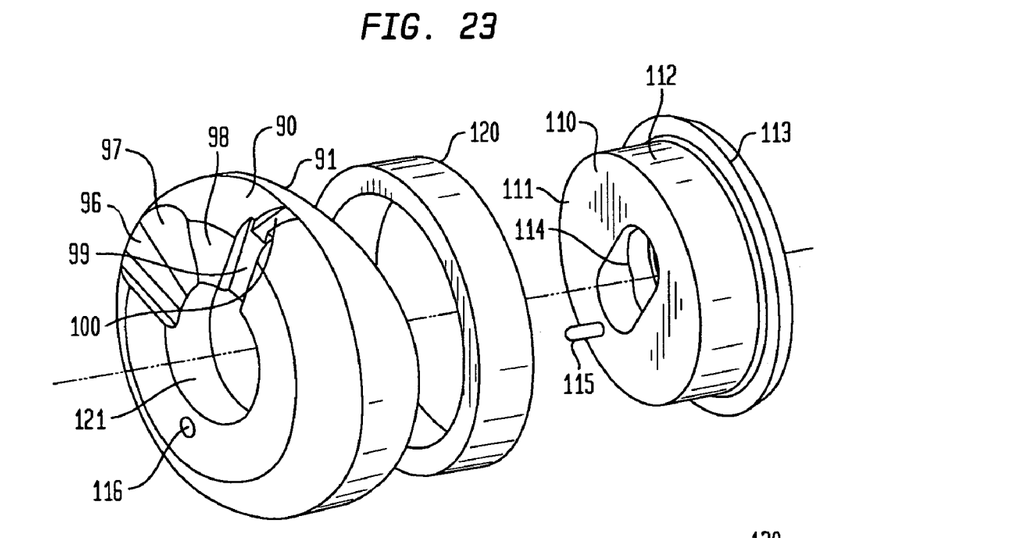
FIG. 23 is a exploded isometric view of the various parts which make up an alternative construction of an adjustable cup holder.

FIGS. 20 and 22 show a construction in which the same reference numerals are used to indicate similar parts as in FIGS. 17 to 19 and the constructions of the handle 4 is generally similar to that described in FIGS. 17, 18 and 19 but the operating trigger lever can be moved to three operative positions. The operating trigger lever is indicated by reference numeral 81 and its cams, indicated by reference numeral 82, have three operating surfaces, indicated by reference numerals 83, 84 and 85 respectively.

FIG. 20 shows the operating trigger lever 81 in a first position where the cam surface 83 bears against the cylindrical bearing block 67 on the hand wheel 68. In this position the flexible element can be assembled onto the handle.

Before assembling the cup holder 1 to the end piece on the extension 5 the hand wheel 68 is tightened up to the cam surface 83 and the operating trigger lever 81 is then moved to the second position, as shown in FIG. 21, and the second cam surface 84 bears against the cylindrical bearing block 67. This cam surface is 1.5 mm lower than cam surface 83 and allows the adjustable cup holder assembly to be fitted to the end piece of the extension 5 and for the locking head 30 to be located in place.

The assembly is now ready to receive the cup with which it is to be used.

When the cup is placed in position on the adjacent cup holder 1 the operating trigger lever 81 is moved to the third position as shown in FIG. 22. This causes cam surface 85 to engage the cylindrical bearing block 67 and thus tension the flexible element 3. The cam surface 85 is 1 mm higher than the cam surface 84 and this provides sufficient tensioning in the flexible element 3 to compress the flexible ring 23 to cause it to expand and grasp the rim of the cup.

Due to the dimensions of the cam surface this now allows the surgeon 0.5 mm movement if he wishes to further tighten the grip on the cup by operating the hand wheel 68.

To release the cup the operating trigger lever 81 is moved back to the position shown in FIG. 21 which allows the release of the inserter from the cup and the operating trigger lever can be moved further counterclockwise to a position shown in FIG. 20 to allow the various parts of the cup holder 1 to be released from the end piece 15.

As described above, the construction as shown in FIGS. 17 to 21 can be used with the arrangements shown in FIGS. 7 to 15.

FIGS. 19 to 28 show an alternative form of releasable cup holder which can not only be used with the construction shown in FIGS. 17 to 22 but also with the arrangement shown in FIGS. 1 to 8. In this construction the releasable cup holder comprises a backing member 90 which has an outer rim 91 shaped and adapted to align with the outer rim of the acetabular cup to be inserted. The backing member 90 is adapted for use with an end piece 92 as shown in FIGS. 19, 24, 25 and 26. This end piece, which is rigidly secured to the hollow extension 5, has a substantially flat circular bearing surface 93 similar to the bearing surface 16 of the construction shown in FIGS. 7 and 8. It also has a pair of spaced apart shaped abutments 94 which are arranged diametrically opposed to each other on each side of a bore which communicated through the bore of the hollow extension 5.

Figure 24:
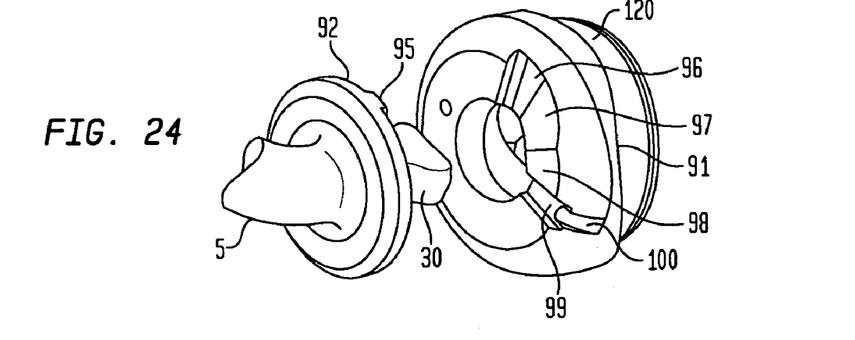
FIG. 24 shows the parts illustrated in FIG. 23 assembled together and ready for assembly onto a shaped end piece on the handle and stem.
Figure 25:
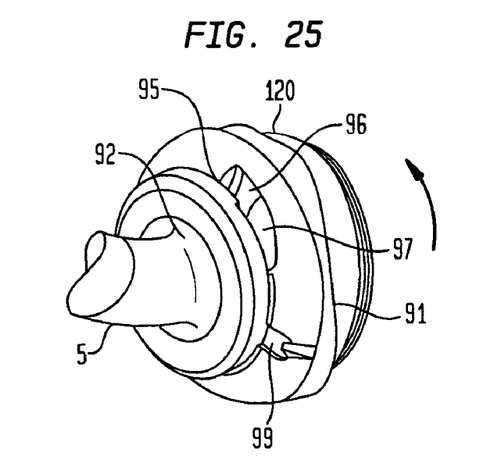
FIG. 25 shows the parts shown in FIGS. 23 and 24 in position and ready for rotation to a locked position.
Figure 26:
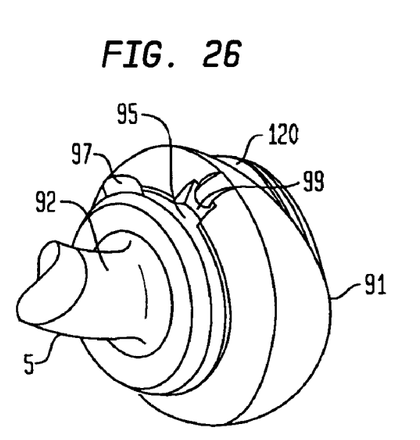
FIG. 26 shows the parts locked in position on the handle and stem.

In addition to the abutments 94 the end piece 92 has a projection 95 adjacent its outer rim and best seen in FIGS. 24, 25 and 26 and a shaped locking head 30, similar to that shown in the other constructions, is also provided.

The backing member 90 has a first radial groove 96 from which extends a ramp 97. This terminates in a flat circumferentially extending surface 98 and leads to a second radially extending groove 99 with which is aligned a cut-out 100.

The movable operating member 110 in this construction comprises a flanged circular plate 111 the flange 112 having a radially projecting rim 113. A shaped opening 114, similar to the shaped opening 26 in the construction shown in FIGS. 7 to 12, is provided and the circular plate 111 has a projecting pin 115.

The flexible element 120 in this arrangement is shaped to extend over the flange 112 and rest against the outer rim 113.

This construction is assembled by placing the flexible element 120 in position on the flange 112 and pushing the operating member 110 onto the backing member 90, at the same time engaging the pin 115 in a bore 116 in the backing member. It will be appreciated that the pin 115 aligns and holds the parts together. The assembled parts are presented to the end piece 92 as shown in FIG. 24 and then pressed against the end piece 92 as shown in FIG. 25. The flexible element is dimensioned so that it is slightly compressed when the parts are pushed into positions as shown in FIG. 25 with first groove 96 aligned with the projection 95 on the end piece 92. The parts are now rotated in the direction of the arrow shown in FIG. 25 moving the projection 95 up the ramp 97 and around until it engages the second groove 99 as shown in FIG. 26.

Prior to assembling the parts onto the end piece 92 the operating trigger lever 81 of the construction shown in FIG. 19 or FIGS. 20 to 22 is moved to the free position. With the construction shown in FIG. 19 the hand wheel 68 is rotated to a position in which there is maximum movement and the handle is then closed which produces a reduced tension force and enables the end piece 30, which has been passed through a circular opening 121 in the backing member 90 and through the shaped opening 114 in the movable operating member 110 which acts to hold the parts in position.

In the construction shown in FIGS. 20, 21 and 22 this position is achieved by moving the operating trigger lever 81 to its first tension position.

Figure 27:
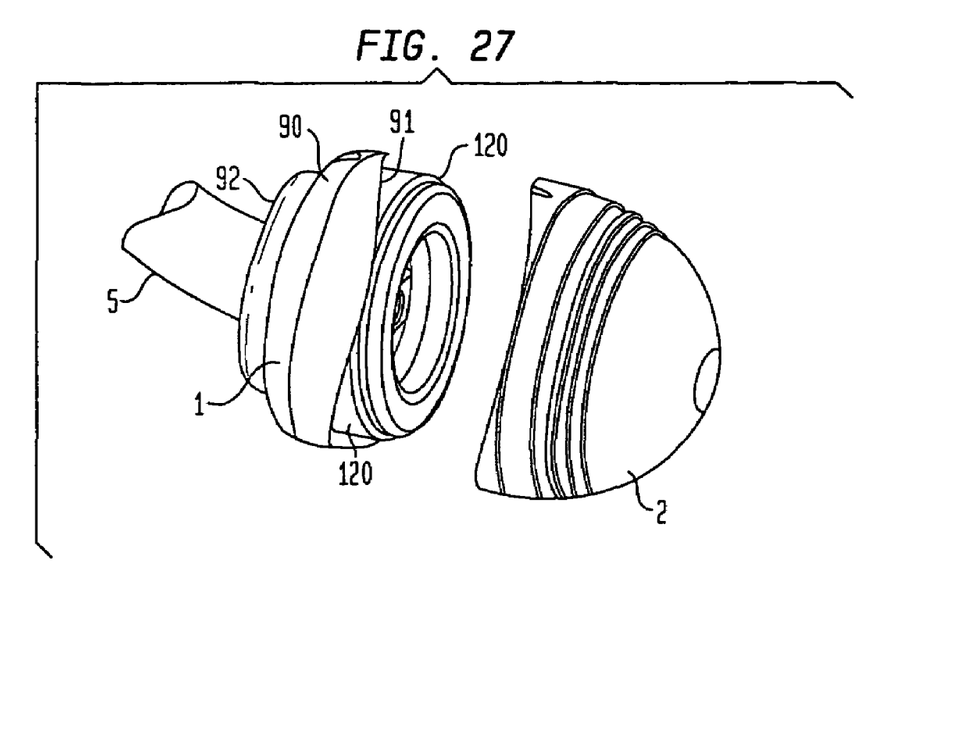
FIG. 27 is an isometric view of the parts shown in FIGS. 23 to 26 in position on the handle and stem and ready to receive the acetabular cup which is to be used.
Figure 28:
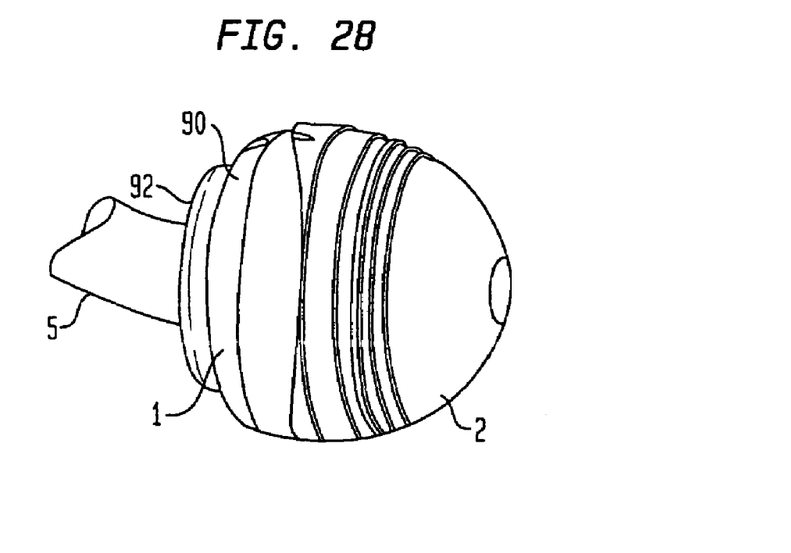
FIG. 28 is a view similar to view 27 with the acetabular cup in place on the inserter.

The inserter is now assembled and ready to receive the cup 2 with which it is to be used. The shaped cup is aligned with the shaped edge 91 of the backing member 90 as shown n FIG. 27. The cup is then placed onto the cup holder 1 as shown in FIG. 28 with the flexible element within the outer rim of the cup in a similar manner to that described with the earlier embodiments.

When used with the arrangement shown in FIGS. 17 to 19 the adjustment hand wheel is adjusted to provide maximum tension in the flexible element 3 and operating trigger level 60 is then moved to provide the maximum tension of the flexible elements 3 which thus acts to expand the flexible ring 120 by compressing it between the backing member 90 and the operating member 110, the ring thus expanding radially to grasp the cup 2.

It will be understood that the flexible ring 23 now performs two functions. It not only provides a resilient bias to hold the parts in position when they are first located on the end piece 92 but, on further compression, it also acts to grasp the cup 2.

A number of alternative cup holders can be provided of different dimensions for use with cups of different dimensions so that a modular construction is achieved. Thus, one handle and extension can be used with a large number of different shaped and sizes adjustable cup holders.

The various parts can be made from any convenient material, for example the various parts of the adjustable cup holder can be made from metal or a synthetic plastics material. Again, the handle and extension can be metal or a synthetic plastics material as can the end piece. It is also possible to use different materials for the other parts, for example the flexible element could be made from a suitably strong synthetic material as well as from metal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic acetabular cup inserter comprising a handle; an extension coupled to the handle at a first end thereof; an elongated flexible element mounted within the extension coupled adjacent the handle at a first end thereof; an adjustable cup holder mounted at a second end of the extension having an expandable element which can expand radially to grasp an acetabular cup; the elongated flexible element extending in the extension from the handle to the cup holder and coupled to the expandable element at a second end of the flexible element; a means mounted adjacent the handle for tensioning said flexible element to cause the expandable element to expand.

2. The prosthetic acetabular cup inserter as claimed in claim 1 in which the adjustable cup holder is carried on the extension and the elongated flexible element is tensioned adjacent the handle.

3. The prosthetic acetabular cup inserter as claimed in claim 2 in which the handle is connected to the adjustable cup holder by a hollow extension.

4. The prosthetic acetabular cup inserter as claimed in claim 3 in which the elongated flexible element is carried within the hollow extension.

5. The prosthetic acetabular cup inserter as claimed in claim 4 in which the extension is curved.

6. The prosthetic acetabular cup inserter in claim 1 in which the tension is applied to the elongated flexible element by an operating element carried on a ramp or a screw thread so that rotation thereof causes lengthwise movement of the elongated flexible element.

7. The prosthetic acetabular cup inserter in claim 1 in which the tension is applied to the elongated flexible element by a pivoted trigger mechanism, angular movement of which causes lengthwise movement of the elongated flexible element.

8. The prosthetic acetabular cup inserter as claimed in claim 7 including means for adjusting the operative length and tension of the elongate flexible element.

9. The prosthetic acetabular cup inserter as claimed in claim 7 in which the trigger mechanism is coupled to a rotatable cam which can be operated to apply tension to the elongate flexible element.

10. The prosthetic acetabular cup inserter as claimed in claim 1 in which the expandable element is made from an elastomeric material.

11. The prosthetic acetabular cup inserter as claimed in claim 10 in which the expandable element is axially compressed to cause it to expand radially to grasp the cup.

12. The prosthetic acetabular cup inserter as claimed in claim 11 in which the adjustable cup holder includes a backing member and a movable operating member to which the expandable element is connected and between which a resilient ring is located so that it is axially compressed when the movable operating member is moved towards the backing member when tension is applied to the flexible element.

13. A prosthetic acetabular cup inserter as claimed in claim 1 in which the expandable element is in the form of a split ring.

14. The prosthetic acetabular cup inserter as claimed in claim 13 in which the cup holder includes a backing member and a movable operating member which has a tapered portion which can act against an inner surface of the split ring to cause the ring to radially expand to engage and grasp the cup to be inserted.

15. The prosthetic acetabular cup inserter as claimed in claim 1 in which the flexible element is made as a metal cable.

16. The prosthetic acetabular cup inserter as claimed in claim 1 including a combination therewith one or more alternative cup holder which have different dimensions and are for use with cups of different dimensions from a first cup and which can be fitted in place of said first cup.

17. The prosthetic acetabular cup inserter as claimed in claim 1 in which the cup holder is provided with a landmark to include the position of the cup in relation to a marking on the rim of an acetabulum with which the inserted cup is to be used.

18. An acetabular cup inserter comprising:
a handle;
a hollow curved shaft having a first end coupled to the handle and a second end and a flexible cable extending therebetween within a hollow portion of said shaft;
a radially expandable elastomeric ring at said second end of the shaft having at outer surface for engaging an internal surface of the acetabular cup said ring including an expansion means connected to said cable for engaging an inner surface of the ring and expanding the ring; and
an actuation means adjacent the handle for applying tension to said cable, said tension causing the expansion means to expand said ring.

19. The acetabular cup inserter of claim 18 wherein said actuation means is a trigger mounted on the handle at said first shaft end, said trigger pivotally connected to said handle.

20. An acetabular cup outer shell inserter/impactor comprising:
a first end having a handle, said end including a wire coupling element;
a cup shell insertion end opposite said first end having a radially expandable element for contacting an inner surface of the acetabular cup shell;
a curved tubular shaft portion extending between said handle end and said insertion end;
a wire having a first end coupled to said coupling element at said first end extending through said tubular shaft portion and into said insertion end, said wire having a second end coupled to a means for radially expanding the expandable element;
a means for applying tension to said wire, the tension causing the wire to move towards said first end and causing the expandable element to expand and grip the inner surface of the shell.

21. A prosthetic acetabular cup inserter comprising an adjustable cup holder having a resilient ring which can expand to grasp the cup with which it is to be used by operation of an elongated flexible cable including a means for tensioning the flexible element to cause the resilient ring to expand, the adjustable cup holder is carried on an operating handle and the elongated flexible cable is operated from the handle, the handle is connected to the adjustable cup holder by a curved extension, the elongated flexible cable being carried within the curved extension.

22. A prosthetic acetabular cup inserter comprising an adjustable cup holder having a resilient ring which can extend to grasp the cup with which it is to be used by operation of an elongated flexible cable characterized by a means for tensioning said flexible cable to cause the resilient ring to expand, the tension is applied to the elongated flexible element by an operating element carried on a ramp or a screw thread so that rotation thereof causes lengthwise movement of the elongated flexible element.

23. A prosthetic acetabular cup inserter comprising an adjustable cup holder having a resilient ring which can extend to grasp the cup with which it is to be used by operation of an elongated flexible cable characterized by a means for tensioning said flexible cable to cause the resilient ring to expand, the tension is applied to the elongated flexible element by a pivoted trigger mechanism, angular movement of which causes lengthwise movement of the elongated flexible element.

24. A prosthetic acetabular cup inserter comprising an adjustable cup holder having a resilient ring which can extend to grasp the cup with which it is to be used by operation of an elongated flexible cable characterized by a means for tensioning said flexible cable to cause the resilient ring to expand, the resilient ring is made from an elastomeric material, the elastomeric ring is axially compressed to cause it to expand radially to grasp the cup, the adjustable cup holder includes a backing member and a movable operating member to which the flexible element is connected and between which the resilient ring is located so that it is axially compressed when the movable operating member is moved towards the backing member when tension is applied to the flexible element.

25. A prosthetic acetabular cup inserter comprising an adjustable cup holder having a resilient ring which can extend to grasp the cup with which it is to be used by operation of an elongated flexible cable characterized by a means for tensioning said flexible cable to cause the resilient ring to expand, the flexible element is made as a metal cable.

26. A prosthetic acetabular cup inserter comprising an adjustable cup holder having a resilient ring which can extend to grasp the cup with which it is to be used by operation of an elongated flexible cable characterized by a means for tensioning said flexible cable to cause the resilient ring to expand, including in combination therewith one or more alternative cup holder which have different dimensions and are for use with cups of different dimensions from a first cup and which can be fitted in place of said first cup.

27. The prosthetic acetabular cup inserter as claimed in claim 24 in which the adjustable cup holder is shaped and dimensioned so that the resilient ring is adapted to grasp the inner rim of the cup with which it is used or an area adjacent thereto.

28. The prosthetic acetabular cup inserter as claimed in claim 24 in which the backing member is removably secured to the handle or extension thereof to allow the cup holder to be removed.

29. The prosthetic acetabular cup inserter as claimed in claim 28 in which the backing member is provided with a means for securing it in a predetermined angular position in relation to an axis of the handle and/or extension thereof.

30. The prosthetic acetabular cup inserter as claimed in claim 28 in which the resilient ring also acts to resiliently bias the movable operating member and the backing member apart to hold them in position when initially located on the handle or extension.

31. The prosthetic acetabular cup inserter as claimed in claim 24 including means to apply a first tension to the flexible cable to hold the backing member and moveable operating member in position in the adjustable cup holder and then to apply a second tension to cause the resilient ring to expand.

32. The prosthetic acetabular cup inerter as claimed in claim 31 further comprising a trigger for applying tension to the cable in which the first tension is achieved in a first position of said trigger and the second position when the trigger is in a second position.

* * * * *